US012797005B2

(12) United States Patent
Kim et al.

(10) Patent No.: US 12,797,005 B2
(45) Date of Patent: Nov. 17, 2026

(54) POSTURE BALANCE MEASUREMENT SYSTEM AND POSTURE BALANCE MEASUREMENT METHOD USING THE SAME

(71) Applicant: OSONG MEDICAL INNOVATION FOUNDATION, Cheongju-si (KR)

(72) Inventors: Young Jin Kim, Cheongju-si (KR); Seung Pyo Kim, Gwangju (KR); Dong Jun Moon, Sejong (KR); Ha Chul Jung, Cheongju-si (KR); Jin Woo Ahn, Cheongju-si (KR)

(73) Assignee: OSONG MEDICAL INNOVATION FOUNDATION, Cheongju-si (KR)

(*) Notice: Subject to any disclaimer, the term of this patent is extended or adjusted under 35 U.S.C. 154(b) by 202 days.

(21) Appl. No.: 18/839,535

(22) PCT Filed: Feb. 28, 2022

(86) PCT No.: PCT/KR2022/002876

§ 371 (c)(1),
(2) Date: Aug. 19, 2024

(87) PCT Pub. No.: WO2023/163256

PCT Pub. Date: Aug. 31, 2023

(65) Prior Publication Data

US 2025/0160735 A1 May 22, 2025

(51) Int. Cl.
*A61B 5/00* (2006.01)
*A61B 5/103* (2006.01)

(52) U.S. Cl.
CPC .......... *A61B 5/4561* (2013.01); *A61B 5/1036* (2013.01); *A61B 5/6892* (2013.01)

(58) Field of Classification Search
CPC ................ A61B 5/4561; A61B 5/1036; A61B 5/6892; A61B 5/1038; A61B 5/4023
See application file for complete search history.

(56) References Cited

U.S. PATENT DOCUMENTS

| | | | |
|---|---|---|---|
| 7,972,246 B2 | 7/2011 | Shinomiya et al. | |
| 2006/0247104 A1 | 11/2006 | Grabiner et al. | |

(Continued)

FOREIGN PATENT DOCUMENTS

| | | | | |
|---|---|---|---|---|
| CN | 112790951 A * | 5/2021 | ............... A61H 3/02 |
| KR | 20090027039 A | 3/2009 | |

(Continued)

OTHER PUBLICATIONS

Extended European Search Report issued on Aug. 11, 2025.
International Search Report issued on Nov. 18, 2022.

*Primary Examiner* — Eric F Winakur
*Assistant Examiner* — Sienna C Pyle
(74) *Attorney, Agent, or Firm* — LEEPI

(57) ABSTRACT

In a posture balance measurement system and a posture balance measurement method using the system, the system includes a plate, a first pressure measuring part, a support frame, a second pressure measuring part, a calculating part and a control decision part. A subject is located with standing upright on the plate. The first pressure measuring part is disposed on the plate, and is configured to measure a plantar pressure of the subject. The subject holds the support frame. The second pressure measuring part is disposed on the support frame, and is configured to measure a load applied to the support by the subject. The calculating part is configured to calculate a balance score in each posture of the subject, based on the measured plantar pressure and the load. The control decision part is configured to decide whether the subject has a disability, based on the balance score.

9 Claims, 7 Drawing Sheets

(56) References Cited

U.S. PATENT DOCUMENTS

| | | | | |
|---|---|---|---|---|
| 2015/0173652 | A1 | 6/2015 | Brunner | |
| 2015/0305656 | A1* | 10/2015 | Takehara ............. | A61B 5/4023 600/595 |
| 2020/0406097 | A1 | 12/2020 | Otsuki et al. | |

FOREIGN PATENT DOCUMENTS

| | | | |
|---|---|---|---|
| KR | 100921513 | B1 | 10/2009 |
| KR | 20160025879 | A | 3/2016 |
| KR | 20190012986 | A | 2/2019 |
| KR | 102270146 | B1 | 6/2021 |
| KR | 20220051451 | A | 4/2022 |

* cited by examiner

POSTURE BALANCE MEASUREMENT SYSTEM AND POSTURE BALANCE MEASUREMENT METHOD USING THE SAME

BACKGROUND

1. Field of Disclosure

The present disclosure of invention relates to a posture balance measurement system and a posture balance measurement method using the system, and more specifically the present disclosure of invention relates to a posture balance measurement system and a posture balance measurement method using the system, configured to measure balancing function of the subject using a pressure of a pressure plate on which the subject is positioned and a pressure of a handle held by the subject, for testing the subject's balancing function such as dizziness.

2. Description of Related Technology

Generally, the sensory organization test uses the center of pressure of the footrest to selectively apply stimuli under a total of 6 conditions for visual, somatic, and tactile sensations, and judges the result based on the equilibrium score in each condition.

The sensory organization test is a representative test method for examining equilibrium functions such as dizziness. For example, as disclosed in Korean Patent No. 10-0921513, in the sensory organization test, a number of test methods are applied in which the test is performed by measuring only the plantar pressure using a plantar pressure measuring device.

However, in the case of testing such equilibrium function only with the plantar pressure of the footrest where the subject is located, the subject may be separated from the footrest during the examination process, or may lean on a support such as a safety device or a wall located near the examination device, if the subject is elderly or has severe symptoms of dizziness or psychological instability. Thus, when this situation occurs, an error in the measured equilibrium score may occur, and a problem of an increase in inspection time may be caused.

Accordingly, there is a problem in that the balance function test result is not accurate by simply measuring plantar pressure while the subject is positioned on the footrest, and repeated measurements are required, causing inconvenience and inefficiency to both the subject and the examiner.

Related prior art is Korean Patent No. 10-0921513.

SUMMARY

The present invention is developed to solve the above-mentioned problems of the related arts. The present invention provides a posture balance measurement system capable of measure balancing function of the subject using a pressure of a pressure plate on which the subject is positioned and a pressure of a handle held by the subject, for testing the subject's balancing function such as dizziness, so that a more accurate examination may be performed and the subject's body may be fixed and measured at the same time without installing a separate measurement module.

In addition, the present invention also provides a posture balance measurement method using the system.

According to an example embodiment, the system includes a plate, a first pressure measuring part, a support frame, a second pressure measuring part, a calculating part and a control decision part. A subject is located with standing upright on the plate. The first pressure measuring part is disposed on the plate, and is configured to measure a plantar pressure of the subject. The subject holds the support frame. The second pressure measuring part is disposed on the support frame, and is configured to measure a load applied to the support by the subject. The calculating part is configured to calculate a balance score in each posture of the subject, based on the measured plantar pressure and the load. The control decision part is configured to decide whether the subject has a disability, based on the balance score.

In an example, the support frame may include a left support frame and a right support frame respectively positioned at both sides of the subject. The second pressure measuring part may include a left second pressure measuring part configured at the left support frame and a right second pressure measuring part configured at the right support frame.

In an example, the system may further include an information input part configured to receive a body information of the subject, a position measuring part configured to measure a standing position of the subject on the plate, and a posture control part configured to control a posture of the subject, based on the standing position of the subject and the holding position of the subject on the support frame.

In an example, the posture control part may be configured to change a height of the support frame.

In an example, the calculating part may be configured to calculate a center of the pressure due to the plantar pressure (COP AP position), based on the measured plantar pressure, and to calculate a center of the pressure due to the load (COP loadcell position), based on the measured load.

In an example, the calculating part may be configured to obtain an information on a movement of a center of gravity of a subject's body, based on the center of the pressure due to the plantar pressure and the center of the pressure due to the load. The information on the movement of the center of gravity may be obtained with coordinate values on a plane.

In an example, the calculating part may be configured to obtain an inclination angle of a subject's body, based on the center of the pressure due to the plantar pressure, the center of the pressure due to the load and a center of foot of the subject. The calculating part may be configured to calculate the balance score based on a maximum value and a minimum value of the inclination angle.

In an example, the inclination angle (θ) may be defined by Equation (2), $$\theta = \sin^{-1}\frac{P}{H} - 2.3 \quad \text{Equation (2)}$$

the balance score (Score) may be defined by Equation (3), $$\text{Score} = \frac{12.5 - (\theta_{max} - \theta_{min})}{12.5} \times 100 \quad \text{Equation (3)}$$

here, P may be defined by Equation (4)

$$P = (COP\ AP \text{ position} - \text{Center of foot}) - COP\ loadcell \text{ position}) \quad \text{Equation (4)}$$

H may be a distance from a plantar region to the center of gravity of the subject when the subject is in a normal standing state, $\theta_{max}$ may be a maximum value of the inclination angle, and $\theta_{min}$ may be a minimum value of the inclination angle.

According to another example embodiment, the method includes measuring a plantar pressure of a subject, at a first pressure measuring part disposed on a plate on which the subject is located with standing upright, measuring a load, at a second pressure measuring part disposed on a support frame held by the subject, calculating a balance score in each posture of the subject, based on the measured plantar pressure and the load, and deciding whether the subject has a disability, based on the balance score.

In an example, in the calculating the balance score, an information on a movement of a center of gravity of a subject's body may be obtained based on a center of the pressure due to the plantar pressure and a center of the pressure due to the load, and the information on the movement of the center of gravity may be obtained with coordinate values on a plane.

In an example, the calculating the balance score may include obtaining an inclination angle of a subject's body, and calculating the balance score based on a maximum value and a minimum value of the inclination angle.

In an example, the obtaining the inclination angle may include calculating a center of the pressure due to the plantar pressure, based on the measured plantar pressure, calculating a center of the pressure due to the load, based on the measured load, and obtaining the inclination angle of the subject's body, based on the center of the pressure due to the plantar pressure, the center of the pressure due to the load and a center of foot of the subject.

In an example, before measuring the plantar pressure, the method may include obtaining a body information of the subject, measuring a standing position of the subject on the plate, and controlling a posture of the subject, based on the standing position of the subject and the holding position of the subject on the support frame.

According to the present example embodiments, conventionally, when balance function is tested simply using a plantar pressure, the subject is unable to support the body. However, using the load generated as the subject holds and supports, in addition to the plantar pressure of the subject, the safety of the user may be improved during the test, the accuracy of the test results may be improved and the test time may be decreased.

The inclination angle of the subject' body is obtained by the center of the pressure due to the plantar pressure, the center of the pressure due to the load and the center of foot of the subject, and then the balance score is calculated. Thus, the obtained balance score may be more accurate.

A support frame is provided so that the subject may support his or her body in an uncomfortable situation, and by using a load that is naturally applied while supporting the body on the support frame for the test, the accuracy of the test results for the subject may be further improved.

Here, the height of the support frame is variable based on the position held by the subject and the position in which the subject stands, so that the plantar pressure and the load are measured after placing the subject in a more accurate posture and position for the test. Thus, it is possible to perform optimal tests that suit the physical conditions of various subjects.

Figure 1:
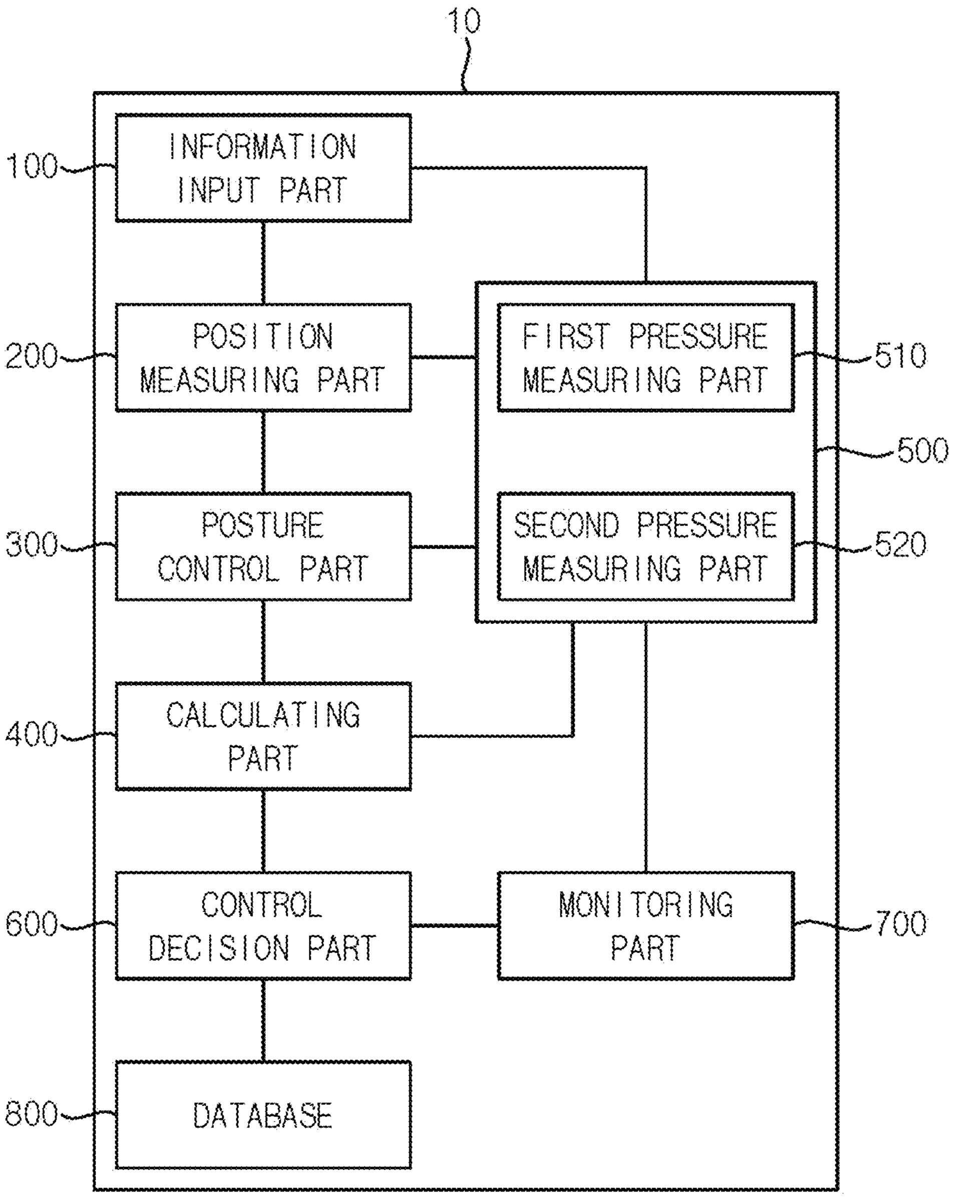
FIG. 1 is a block diagram illustrating a posture balance measurement system according to an example embodiment of the present invention.

| * Reference numerals | |
|---|---|
| 10: | posture balance measurement system |
| 11: | plate |
| 20: | left support frame |
| 30: | right support frame |
| 40: | vertical frame |
| 50: | fixing unit |
| 100: | information input part |
| 200: | position measuring part |
| 300: | posture control part |
| 400: | calculating part |
| 500: | pressure measuring part |
| 600: | control decision part |
| 700: | monitoring part |
| 800: | database |

DETAILED DESCRIPTION

The invention is described more fully hereinafter with Reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. In the drawings, the size and relative sizes of layers and regions may be exaggerated for clarity.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Hereinafter, the invention is described more fully hereinafter with reference to the accompanying drawings, in which embodiments of the invention are shown.

Figure 2:
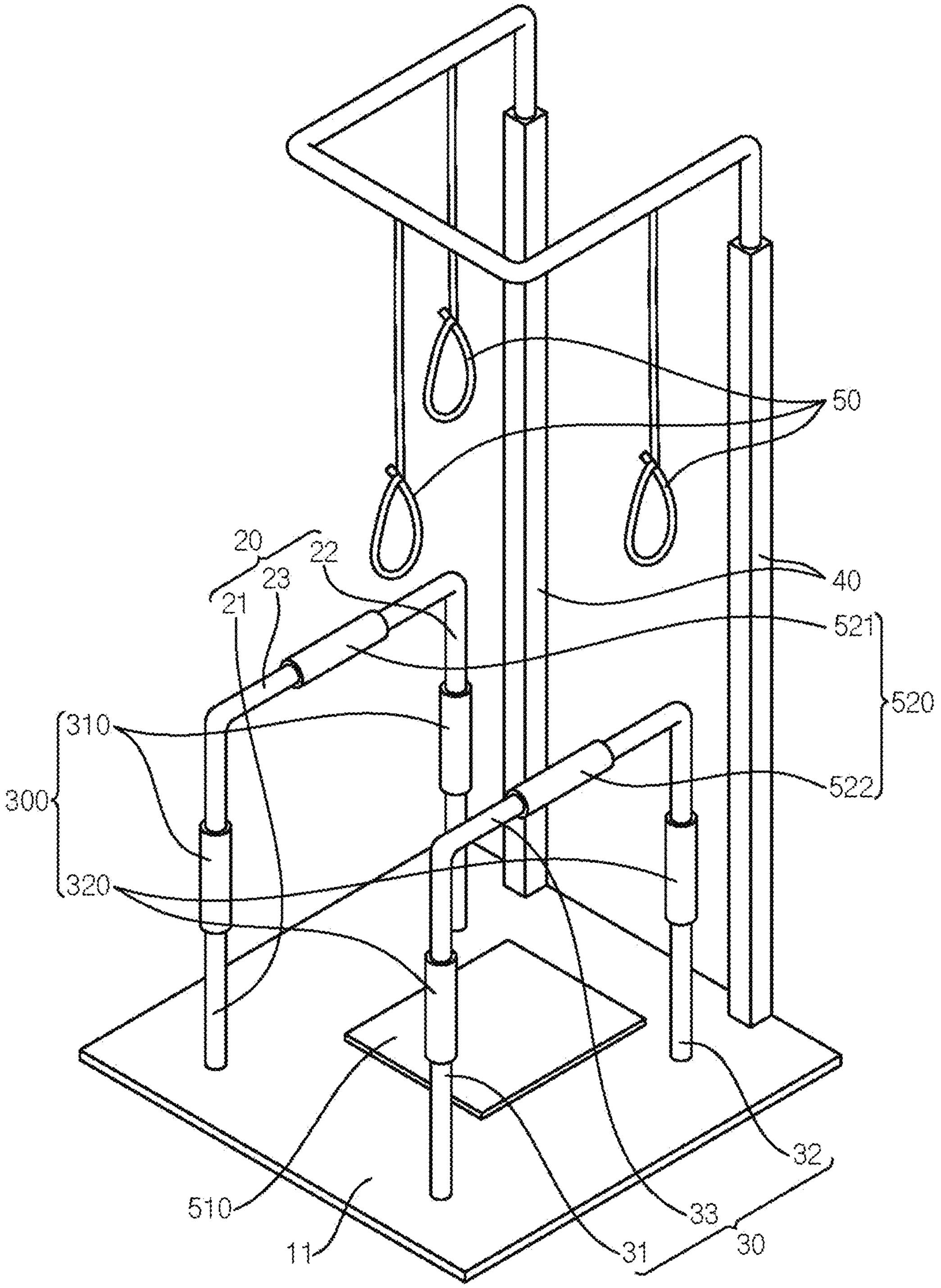
FIG. 2 is a perspective view illustrating an example of the posture balance measurement system of FIG. 1.

FIG. 1 is a block diagram illustrating a posture balance measurement system according to an example embodiment of the present invention. FIG. 2 is a perspective view illustrating an example of the posture balance measurement system of FIG. 1.

Referring to FIG. 1 an FIG. 2 the posture balance measurement system 10 includes a plate 11, a left support frame 20, a right support frame 30, a vertical frame 40, a fixing unit 50, an information input part 100, a position measuring part 200, a posture control part 300, a calculating part 400, a pressure measuring part 500, a control decision part 600, a monitoring part 700 and a database 800.

The plate 11 is located on a base surface, and a first pressure measuring part 510 of the pressure measuring part 500 is positioned on the plate 11.

The left and right support frames 20 and 30, and the vertical frame 40 form a space in which a subject 1 is located, and form a structure at which the fixing unit 50 is fixed. The structure may be configured as illustrated in FIG. 2.

The left and right support frames 20 and 30 are extended from the plate 11, and are disposed at left and right sides of the subject, respectively. The subject may hold and be supported by the left and right support fames 20 and 30.

Here, the left support frame 20 includes a pair of side surface frames 21 and 22 extending upwardly from the plate 11 and spaced apart from each other, and an upper frame 23 connecting the pair of the side surface frames 21 and 22 to each other. The right support frame also includes a pair of side surface frames 31 and 32 extending upwardly from the plate 11 and spaced apart from each other, and an upper frame 33 connecting the pair of the side surface frames 21 and 22 to each other.

A left posture control part 310 is configured at the side surface frames 21 and 22 of the left support frame, and a right posture control part 320 is configured at the side frames 31 and 32 of the right support frame.

In addition, a left second pressure measuring part 521 is configured at the upper frame 23 of the left support frame 20, and a right second pressure measuring part 522 is configured at the upper frame 33 of the right support frame 30.

The vertical frame 40 is positioned at a front side of the left and right support frames 20 and 30, having a height higher than that of each of the left and right support frames 20 and 30. The fixing unit 50 fixed at the vertical frame 40 is positioned toward the subject, and if necessary, a body of the subject may be fixed by the fixing unit 50.

The subject having difficulty standing on his or her own, may be fixed by the fixing unit 50, and then the inspection may be performed.

Here, the shape or the structure of the fixing unit 50 may be variously changed.

Accordingly, using the posture balance measurement system 10 of FIG. 2, the subject places both feet on the first pressure measuring part 510 located on the plate 11, the subject places a left hand on the left second pressure measuring part 521 located on the upper frame 23 of the left support frame 20 and holds the upper frame 23, and the subject places a right hand on the right second pressure measuring part 522 located on the upper frame 23 of the right support frame 30 and holds the upper frame 33. Then, the inspection may be performed.

The information input part 100 receives the body information of the subject. The information input part 100 may receive the body information of the subject to be inspected, based on the body information of the subject stored on the database 800. Alternatively, the body information may be transferred to the information input part 100, with directly inputting the body information by the subject or an assistant.

Here, the body information may be all necessary information for the inspection and not limited including a height, a weight, an age and so on.

The position measuring part 200 measures the standing position of the subject on the plate 11. Here, the subject is standing on the first pressure measuring part 510 located on the plate 11, and then the position measuring part 200 measures the standing position of the subject on the first pressure measuring part 510.

The posture control part 300 includes a let posture control part 310 configured at the side surface frames 21 and 22 of the left support frame 20 with a pair, and a right posture control part 320 configured at the side surface frames 31 and 32 of the right support frame 30.

Here, the posture control part 300 controls the posture of the subject, based on the holding position where the subject holds the upper frames 23 and 33 of the left and right support frames 20 and 30. Here, the measuring results of the position measuring part 200 measuring the standing position of the subject may be considered at the same time.

Generally, since the subject's left and right arm lengths or body skeletons may be different from each other, it is necessary to adjust the arm lengths or body skeletons on both sides within a certain range in order to perform the test described later.

In addition, even when the subject is in a standing position, the subject may be tilted forward or backward, and the degree of this tilt also needs to be adjusted within a certain range.

Accordingly, it is necessary to adjust the subject's posture through the posture control part 300 to within a predetermined range within which the test described later may be performed.

Here, the posture control part 300 includes the left and right posture control parts 310 and 320, and thus the left and right posture may be independently controlled. Each of the left and right posture control parts 310 and 320 is positioned at each of the pair of side surface frames 21, 22, 31 and 32 located in a pair at the front and rear ends respectively, so that the front and rear side postures may be independently controlled.

For example, the posture control part 300 may change a height of each of the side surface frames 21, 22, 31 and 32, to control the posture of the subject.

As explained above, in the pressure measuring part 500, the first pressure measuring part 510 configured at the plate 11 measures a plantar pressure of the subject, and the second pressure measuring part 520 configured at the upper frames 23 and 33 measures a load applied to the upper frames 23 and 33 which is held by the subject and supports the subject.

The first pressure measuring part 510 measures the plantar pressure of the subject, and here, the measured information may include an overall distribution of the plantar pressure of both feet, a range of the plantar pressure, a mean value of the plantar pressure, and so on.

The first pressure measuring part 510 may be a pressure sensor, and a plurality of pressure sensors may be arranged with a predetermined distance and arrangement in an area where both feet are positioned, to measure the distribution of the plantar pressure.

Since the upper frames 23 and 33 includes the left upper frame 23 and the right upper frame 33, a left second pressure measuring part 521 of the second pressure measuring part 520 measures the load applied to the left upper frame 23, and a right second pressure measuring part 522 of the second pressure measuring part 520 measures the load applied to the right upper frame 33.

Here, the second pressure measuring part 520 may be a load cell.

The measured information for the plantar pressure and the load is provided to the calculating part 400.

The monitoring part 700 monitors the measuring state of the posture balance of the subject performed by the posture balance measurement system 10, and if necessary, the monitored information may be displayed or provided to the subject or an operator through a display part.

The calculating part 400 performs a predetermined calculation, based on the plantar pressure measurement results from the first pressure measuring part 510 and the load measurement results from the second measuring part 520, and then calculates a balance score in each posture of the subject and provides the calculated balance score to the control decision part 600.

The control decision part 600 decides whether the subject has a disability, the subject's current condition, and the subject's balance function, based on the calculated balance score. Then, the final decision results and the information may be displayed by the monitoring part 700.

The detailed explanation of the calculation performed in the calculating part 400 is explained below.

Figure 3:
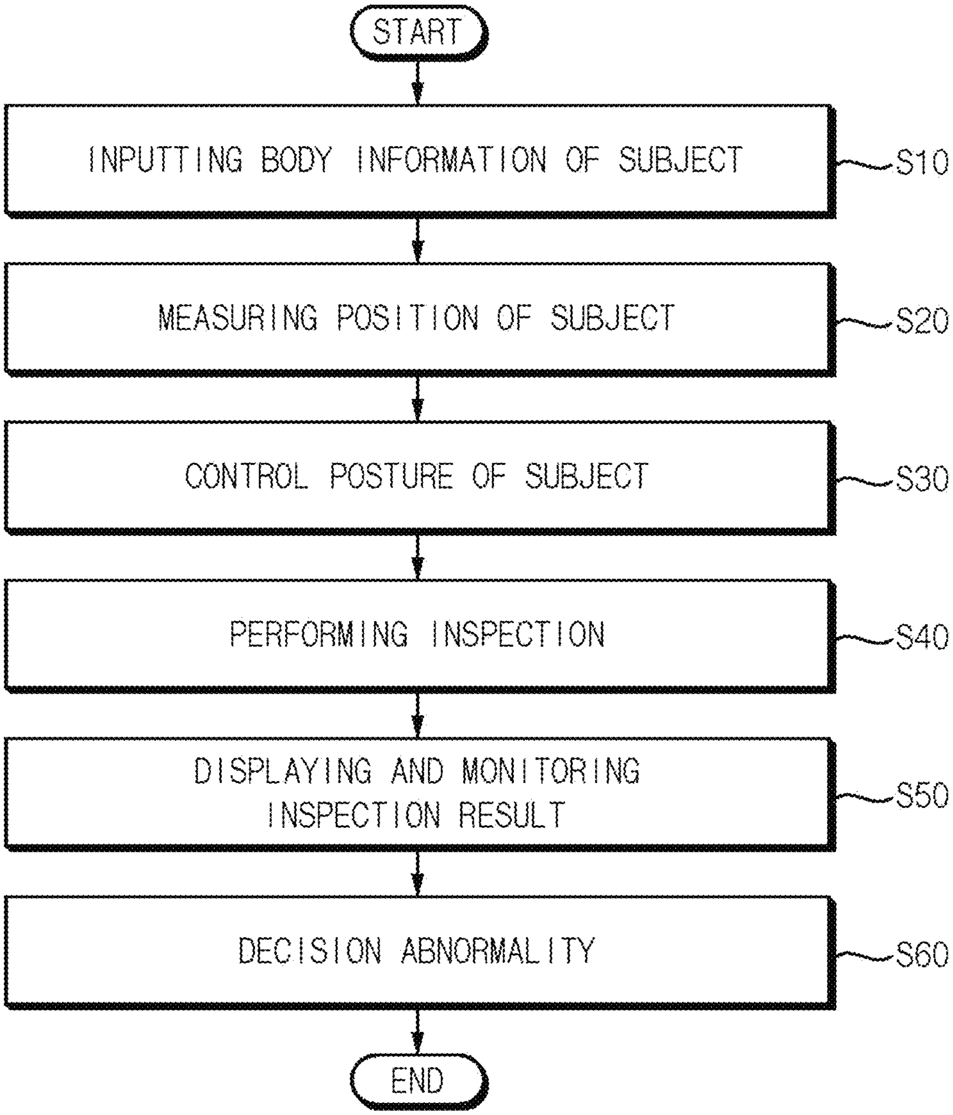
FIG. 3 is a flow chart showing a posture balance measurement method using the system of FIG. 1.

FIG. 3 is a flow chart showing a posture balance measurement method using the system of FIG. 1.

Referring to FIG. 3, in the posture balance measurement method using the system 10, the body information of the subject is inputted to the information input part 100 (step S10).

Here, the body information of the subject is the same as explained above, and the body information may be inputted by an additional terminal or may be provided by confirming the ID of the subject.

Then, when the subject is standing upright on the plate 11, the position measuring part 200 measures the position of the subject standing upright on the plate 11 (step S20).

Here, the subject is standing upright on the plate 11 and holds the left and right support frames 20 and 30, and as explained above, the holding positions of the subject may be different according to the body structure of the subject, the posture of the subject and so on.

Thus, the posture control part 300 controls the posture of the subject, based on the standing position of the subjection and the holding position of the subject on the support frame (Step S30).

Here, the detained control method of the posture control part 300 is the same as explained above.

Then, the inspection, that is, the posture balance of the subject, is performed based on the pressure measurement using the pressure measuring part 500 (step S40).

The monitoring part 700 monitors the measuring state of the subject or the measuring results of the subject and if necessary displays the state or the results (step S50), and the control decision part 600 decides abnormality of the subject based on the measuring results (Step S60).

Hereinafter, referring to FIG. 4 and FIG. 5, the detailed measuring process (step S40) is explained.

Figure 4:
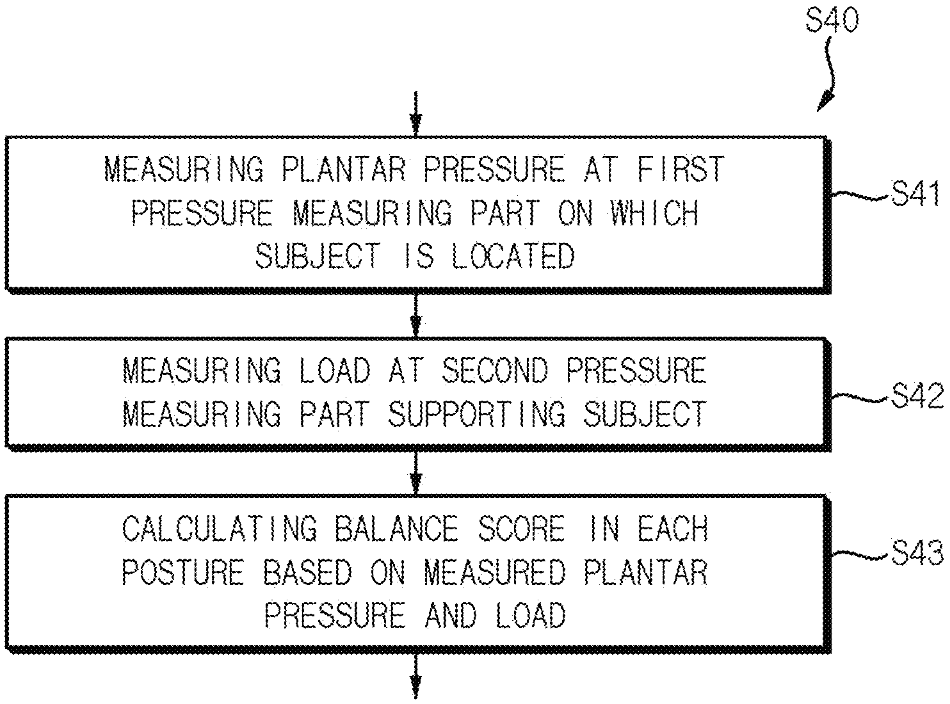
FIG. 4 is a flow chart showing the process of performing inspection of FIG. 3.
Figure 5:
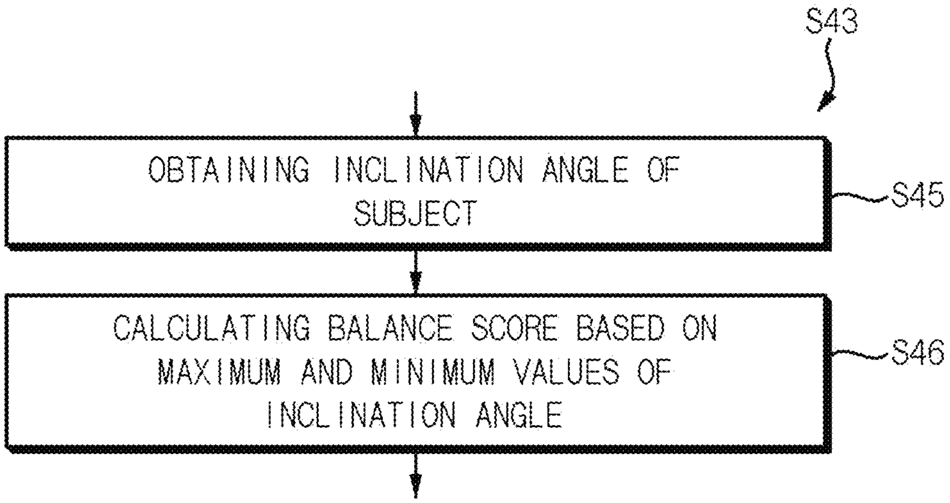
FIG. 5 is a flow chart showing the process of calculating balance score of FIG. 4.
Figure 6A:
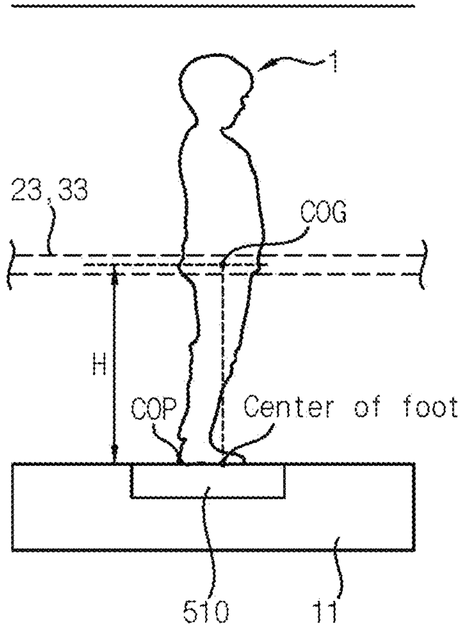
FIG. 6A is a schematic view illustrating a state of standing upright of the subject in the system of FIG. 1.
Figure 6B:
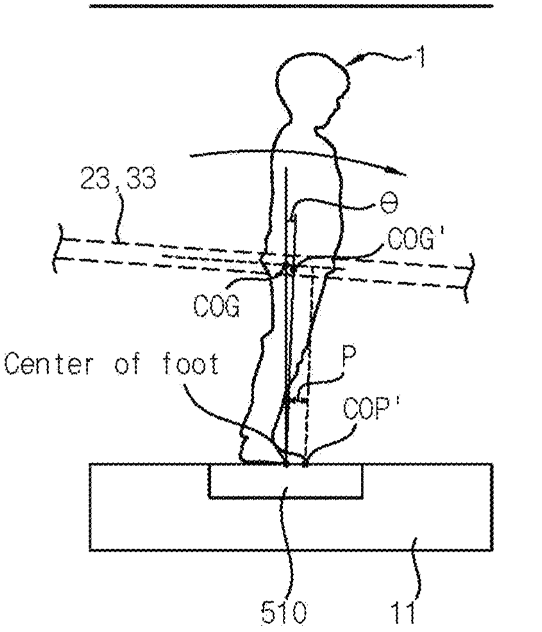
FIG. 6B is a schematic view illustrating a state of inclination of the subject in the system of FIG. 1.

FIG. 4 is a flow chart showing the process of performing inspection of FIG. 3, and FIG. 5 is a flow chart showing the process of calculating balance score of FIG. 4. FIG. 6A is a schematic view illustrating a state of standing upright of the subject in the system of FIG. 1, and FIG. 6B is a schematic view illustrating a state of inclination of the subject in the system of FIG. 1.

Referring to FIG. 4 and FIG. 5, in measuring the posture balance of the subject, the first pressure measuring part 510 disposed on the plate 11 on which the subject is located with standing upright measures the plantar pressure of the subject (step S41).

In addition, the second pressure measuring part 520 configured at the support frame 20 and 30 which is held by the subject and supports the subject measures the load (step S42).

Then, the calculating part 400 calculates the balance score in each posture of the subject, based on the measured plantar pressure measured at the first pressure measuring part 510 and the load measured at the second pressure measuring part 520 (step S43).

Here, to calculate the balance score of the subject, the balance score in each posture should be calculated, with the subject positioned in the six proposed postures. Each posture of the subject for calculating the subject's balance score will be described later with reference to FIG. 8.

In the present example embodiment, the calculating part 400 calculates the balance score based on the plantar pressure and the load, and the detailed calculating process is as follows.

Referring to FIG. 6A and FIG. 6B, in the calculating part 400, an inclination angle of the subject is obtained (step S45), and the balance score "Score" is calculated based on the maximum value ($\theta_{max}$) and the minimum value ($\theta_{min}$) of the obtained inclination angle ($\theta$) (step S46).

In FIG. 6A and FIG. 6B, for the convenience of explanation, the upper frames 23 and 33 of the left and right support frames 20 and 30 are illustrated, and the arms holding the upper frames 22 and 23 are omitted.

Here, in the calculating part 400, a center of the pressure (COP) due to the plantar pressure is calculated based on the measured plantar pressure, and a center of the pressure due to the load is calculated based on the measured load, in obtaining the inclination angle ($\theta$).

Then, in the calculating part 400, the inclination angle of the subject body is obtained, based on the center of the pressure due to the plantar pressure, the center of the pressure due to the load, and a center of foot of the subject.

Here, the center of the pressure (COP) is defined as a point of application of the force when assuming that the pressure distributed over a certain area acts concentrated on one point.

Thus, the center of the pressure due to the plantar pressure may be defined as the point of application of the plantar pressure when assuming that the plantar pressure distributed over a certain area acts concentrated on one point. The center of the pressure due to the load may be defined as the point of action of the load when assuming that the distribution of two different loads of the left and right support frames held and supported by the subject acts concentrated on one point.

The center of foot is defined as center of support for the foot when the subject is supported by the foot and is standing upright normally, and means the center of foot support when considering the overall standing state without considering the pressure actually applied to the foot.

More specifically, referring to FIG. 6A, when the subject 1 is standing upright, the center of the foot of the subject's foot corresponds to the center of the overall standing state, and when the subject 1 is standing upright, the pressure is concentrated on the back of the foot, so the center of pressure (COP) due to the plantar pressure is located on the heel side, as shown.

Here, the center of the foot is generally located in front of the ankle bone of the subject's foot and is located on the front end, which is approximately 14% of the total length of the foot from the front.

In addition, when the subject 1 is standing upright, the center of gravity (COG) of the subject 1 is known to be located at a height of 0.35 to 0.7 times the height of the subject 1, e.g. for example, it may be located at a height of 0.55 times.

As such, assuming that the subject's center of gravity is located at a height of 0.55 times the subject's height, the height H to the subject's center of gravity may be defined by Equation (1) below. Here, $\overline{H}$ is the height of the subject.

$$H = 0.55\overline{H} \qquad \text{Equation (1)}$$

Here, the position of the center of gravity (COG) of the subject 1 corresponds to the center of the pressure (COP) due to the load, that is, the position of the application point of the load, assuming that the distribution of two different loads acts at one point. If the center of pressure (COP) is derived based on the loads measured through the two different left and right second pressure measuring parts 521 and 522, the location of the subject's center of gravity may be derived.

Referring to FIG. 6B, when the subject 1 changes his or her posture by tilting it to a predetermined position to test the balance function, the calculating part 400 may ultimately derive the inclination angle (θ) according to this change in posture through Equation (2) below.

$$\theta = \sin^{-1}\frac{P}{H} - 2.3 \qquad \text{Equation (2)}$$

Here, the inclination angle (θ) is defined to be subtracted by 2.3 from Equation (2) because, in general, the position of the center of gravity (COG) is tilted forward by approximately 2.3 degrees when the subject is standing upright normally. Then, this may be defined differently depending on the subject's titled state.

Further, in the calculating part 400, based on the calculation result of the inclination angle (θ), the final balance score "Score" may be calculated using Equation (3) below.

$$\text{Score} = \frac{12.5 - (\theta_{max} - \theta_{min})}{12.5} \times 100 \qquad \text{Equation (3)}$$

Here, $\theta_{max}$ is the maximum value of the inclination angle (θ), and $\theta_{min}$ is the minimum value of the inclination angle (θ).

In Equation (2), P is defined by Equation (4)

$$P = (COP\ AP\ \text{position} - \text{Center of foot}) - COP\ loadcell\ \text{position}) \qquad \text{Equation (4)}$$

In Equation 4 above, "Center of foot" corresponds to the position of the center of the plantar foot, as previously explained, and is generally located at 14% of the front end of the total length of the foot.

In addition, "COP AP position" is the position shown as COP' in FIG. 6B. As in FIG. 6B, when the subject is inclined in the shear direction shown by the arrow, the distribution of the plantar pressure changes as the subject tilts, and this refers to the center of pressure of the changed plantar pressure.

Further, "COP loadcell position" is the position shown as COG' in FIG. 6B. As in FIG. 6B, when the subject is inclined in the shear direction shown by the arrow, the distribution of the load applied to each wire changes as the subject tilts, and this refers to the center of pressure of the changed load.

As described above, by substituting P derived through Equation (4) into Equation (2), the inclination angle (θ) is calculated, and depending on the subject's condition, the maximum and minimum values of the inclination angle may be derived under predetermined balance test conditions.

Thus, using Equation (3) above, it is finally possible to derive the subject's balance score under certain balance test conditions.

As described above, based on the calculation results of the balance score in the calculating part 400, the control decision part 600 determines whether the subject has a disability, the subject's current status, and furthermore, the subject's balance function (step S60).

Figure 7:
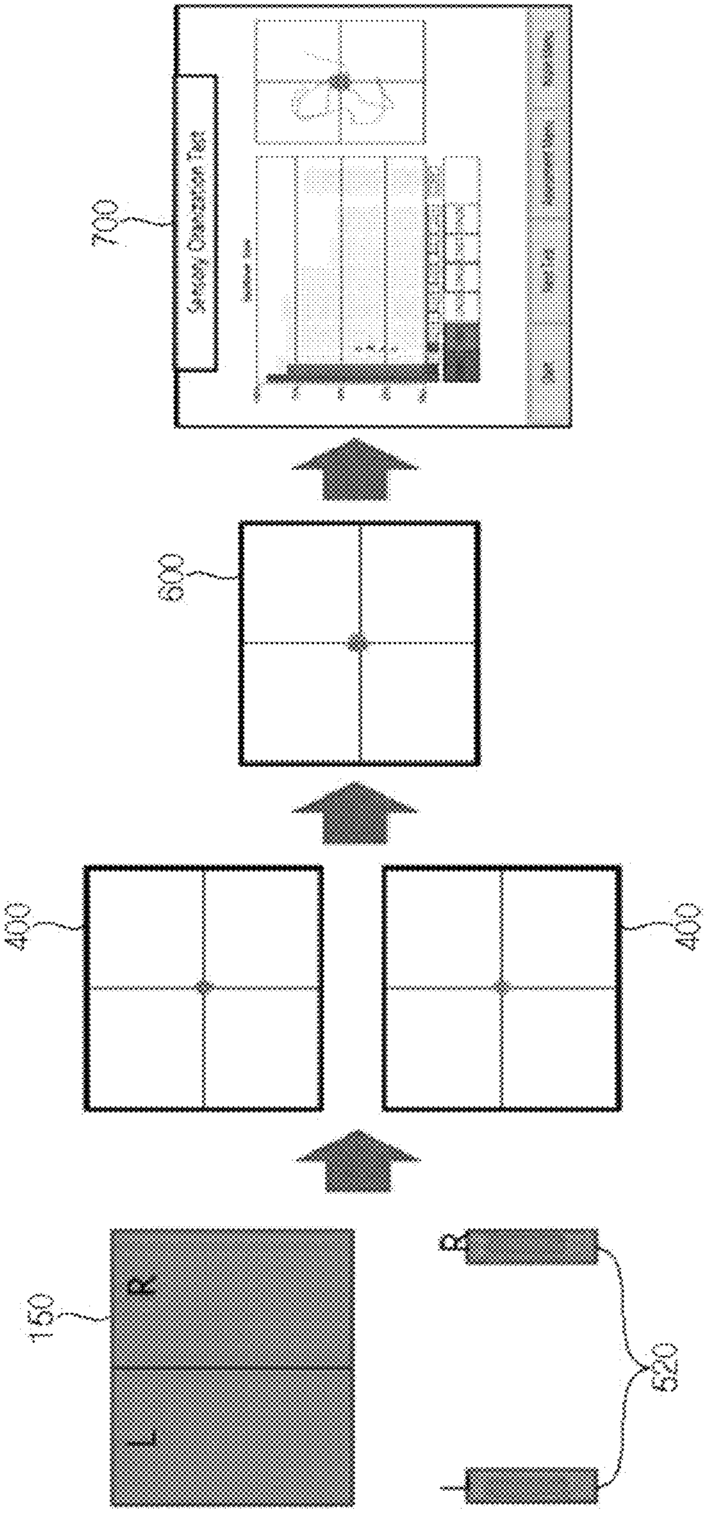
FIG. 7 is a schematic view illustrating an example of measuring the posture balance using the method of FIG. 3.

FIG. 7 is a schematic view illustrating an example of measuring the posture balance using the method of FIG. 3.

Referring to FIG. 7, an example posture balance measurement using the posture balance measurement method is explained.

When the first pressure measuring part 510 measures the plantar pressure of the subject, the calculating part 400 calculates the center of the pressure due to the plantar pressure based on the measured results.

Likewise, the second pressure measuring part 520 measures the load of the support frame 20 and 30, the calculating part 400 calculates the center of the pressure due to the load based on the measured results.

Then, through the calculating process explained above, the calculating part 400 obtains the balance score "Score", and the obtained results are provided to the control decision part 600.

Thus, the decision results on the balance score of the subject in the control decision part 600 are provided to the subject or a user through the monitoring part 700 with various kinds of information. Here, the detailed explanation for obtaining the balance score is explained above and any repeated explanation is omitted.

Alternatively, the calculating part 400 gathers the center of the pressure due to the plantar pressure and the center of the pressure due to the load, and the gathered information is merely provided to the control decision part 600.

Then, the control decision part 600 may obtain the information on the movement of the center of gravity of the subject's body, based on the gathered information, and then the obtained information may be displayed by the monitoring part 700.

Here, the center of the pressure due to the plantar pressure, the center of the pressure due to the load, and the gathered information (the overlapped information) may be displayed with coordinate values on a plane.

Here, the control decision part 600 may obtain simple coordinate values on a two-dimension plane as the balance score, and then the movement of the center of gravity of the subject's body may be obtained based on the coordinate values.

Figure 8:
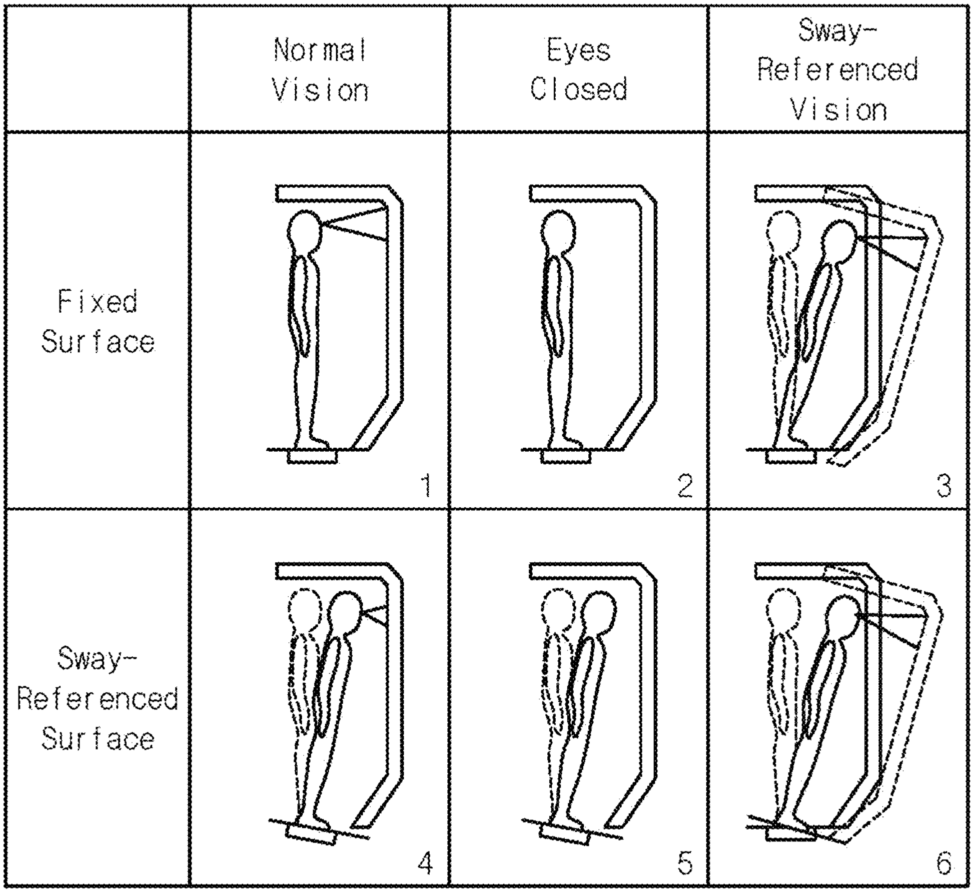
FIG. 8 shows images of 6 conditions used in the sensory organization test.

FIG. 8 shows images of 6 conditions used in the sensory organization test.

The posture balance measurement system and the posture balance measurement method using the system may be applied to the six conditions for a general balance function or perceptual control test in FIG. 8. The state of the subject in each condition may be finally derived as the balance score "Score" through the steps described above, and a judgment may be made regarding the subject's condition.

According to the present example embodiments, when balance function is tested simply using a plantar pressure, the subject is unable to support the body. However, using the load generated as the subject holds and supports, in addition to the plantar pressure of the subject, the safety of the user may be improved during the test, the accuracy of the test results may be improved and the test time may be decreased.

The inclination angle of the subject' body is obtained by the center of the pressure due to the plantar pressure, the center of the pressure due to the load and the center of foot of the subject, and then the balance score is calculated. Thus, the obtained balance score may be more accurate.

A support frame is provided so that the subject may support his or her body in an uncomfortable situation, and by using a load that is naturally applied while supporting the body on the support frame for the test, the accuracy of the test results for the subject may be further improved.

Here, the height of the support frame is variable based on the position held by the subject and the position in which the subject stands, so that the plantar pressure and the load are measured after placing the subject in a more accurate posture and position for the test. Thus, it is possible to perform optimal tests that suit the physical conditions of various subjects Although the exemplary embodiments of the present invention have been described, it is understood that the present invention should not be limited to these exemplary embodiments but various changes and modifications can be made by one ordinary skilled in the art within the spirit and scope of the present invention as hereinafter claimed.

What is claimed is:

1. A posture balance measurement system comprising:
- a plate configured for a subject to stand upright thereon;
- a first pressure measuring part comprising a plurality of pressure sensors disposed on the plate, and configured to measure a plantar pressure of the subject;
- a support frame configured to be held by the subject;
- a second pressure measuring part comprising a load cell disposed on the support frame, and configured to measure a load applied to the support frame by the subject;
- a processor configured to implement a calculating part to calculate a balance score in at least one posture of the subject, based on the measured plantar pressure and the load; and
- the processor being further configured to implement a control decision part to decide whether the subject has a disability, based on the balance score,
- wherein the calculating part is configured to calculate a center of the pressure due to the plantar pressure (COP AP position), based on the measured plantar pressure, and to calculate a center of the pressure due to the load (COP loadcell position), based on the measured load,
- wherein the calculating part is configured to obtain an inclination angle of a subject's body, based on the center of the pressure due to the plantar pressure, the center of the pressure due to the load and a center of foot of the subject,
- wherein the calculating part is configured to calculate the balance score based on a maximum value and a minimum value of the inclination angle.

2. The system of claim 1, wherein the support frame comprises a left support frame and a right support frame configured to be respectively positioned at both sides of the subject,
- wherein the second pressure measuring part comprises a left second pressure measuring part located on the left support frame and a right second pressure measuring part located on the right support frame.

3. The system of claim 1, further comprising:
- an information input part comprising an input terminal configured to receive a body information of the subject;
- a position measuring part comprising a position sensor configured to measure a standing position of the subject on the plate; and
- a posture control part comprising an actuator configured to control a posture of the subject, based on the standing position of the subject and a holding position of the subject on the support frame.

4. The system of claim 3, wherein the posture control part is configured to change a height of the support frame.

5. The system of claim 1, wherein the calculating part is configured to determine information on a movement of a center of gravity of a subject's body, based on the center of the pressure due to the plantar pressure and the center of the pressure due to the load,
- wherein the information on the movement of the center of gravity is determined with coordinate values on a plane.

6. The system of claim 1, wherein the inclination angle (θ) is defined by Equation (2), $$\theta = \sin^{-1}\frac{P}{H} - 2.3 \qquad \text{Equation (2)}$$

wherein the balance score (Score) is defined by Equation (3), $$\text{Score} = \frac{12.5 - (\theta_{max} - \theta_{min})}{12.5} \times 100 \qquad \text{Equation (3)}$$

here, P is defined by Equation (4)

$$P = (COP\ AP\ \text{position} - \text{Center of foot}) - COP\ loadcell\ \text{position}) \qquad \text{Equation (4)}$$

H is a distance from a plantar region to the center of gravity of the subject when the subject is in a normal standing state, θmax is a maximum value of the inclination angle, and Omin is a minimum value of the inclination angle.

7. A posture balance measurement method comprising:

measuring a plantar pressure of a subject, at a first pressure measuring part comprising a plurality of pressure sensors disposed on a plate configured for the subject to stand upright thereon;

measuring a load, at a second pressure measuring part comprising a load cell disposed on a support frame configured to be held by the subject;

calculating. by a processor, a balance score in at least one posture of the subject, based on the measured plantar pressure and the load; and deciding, by the processor, whether the subject has a disability, based on the balance score, wherein the calculating the balance score comprises:

obtaining an inclination angle of a subject's body; and calculating the balance score based on a maximum value and a minimum value of the inclination angle wherein the obtaining the inclination angle comprises:

calculating a center of the pressure due to the plantar pressure, based on the measured plantar pressure;

calculating a center of the pressure due to the load, based on the measured load; and obtaining the inclination angle of the subject's body, based on the center of the pressure due to the plantar pressure, the center of the pressure due to the load and a center of foot of the subject.

8. The method of claim 7, wherein in the calculating the balance score, an information on a movement of a center of gravity of the subject's body is determined based on the center of the pressure due to the plantar pressure and the center of the pressure due to the load, and the information on the movement of the center of gravity is determined with coordinate values on a plane.

9. The method of claim 7, wherein before measuring the plantar pressure, the method comprises:

obtaining a body information of the subject;

measuring a standing position of the subject on the plate; and controlling a posture of the subject, based on the standing position of the subject and the holding position of the subject on the support frame.

* * * * *